United States Patent
Lemaire et al.

(10) Patent No.: US 6,610,875 B1
(45) Date of Patent: Aug. 26, 2003

(54) METHOD FOR PREPARING CHIRAL DIPHOSPHINES

(75) Inventors: Marc Lemaire, Villeurbanne (FR); Rob Tel Halle, Collonges-au Mont -d'Or (FR); Emmanuelle Schulz, Sainte-Foy-les-Lyon (FR); Michel Spagnol, Meyzieu (FR)

(73) Assignees: Rhodia Chimie, Courbevoie Cedex (FR); Centre National de la Recherche Scientifique (CNRS), Paris (FR)

(*) Notice: Subject to any disclaimer, the term of this patent is extended or adjusted under 35 U.S.C. 154(b) by 0 days.

(21) Appl. No.: 09/913,831
(22) PCT Filed: Jan. 14, 2000
(86) PCT No.: PCT/FR00/00083
§ 371 (c)(1), (2), (4) Date: Dec. 11, 2001
(87) PCT Pub. No.: WO00/49028
PCT Pub. Date: Aug. 24, 2000

(30) Foreign Application Priority Data

Feb. 19, 1999 (FR) ............................................ 99 02119

(51) Int. Cl.$^7$ .................................................. C07F 9/50
(52) U.S. Cl. ........................ 558/385; 562/484; 562/480
(58) Field of Search .......................... 558/385; 568/17; 562/480, 484

(56) References Cited

U.S. PATENT DOCUMENTS

| | | | | |
|---|---|---|---|---|
| 5,312,939 A | * | 5/1994 | Hori et al. ..................... | 556/14 |
| 5,621,128 A | * | 4/1997 | Jendralla ...................... | 556/18 |
| 5,693,868 A | * | 12/1997 | Sayo et al. ..................... | 568/8 |
| 5,922,918 A | * | 7/1999 | Zhang et al. .................. | 568/17 |
| 6,075,154 A | * | 6/2000 | Gonda et al. ................ | 549/328 |
| 6,333,435 B1 | * | 12/2001 | Cai et al. ....................... | 568/17 |

FOREIGN PATENT DOCUMENTS

| | | |
|---|---|---|
| WO | WO98/12202 | 3/1998 |
| WO | WO98/42716 | 10/1998 |
| WO | 2099/36397 | 7/1999 |

OTHER PUBLICATIONS

CA:132:264944 abs of Tetrahedron Letters by Re Halle et al 41(5) pp 643–646 Jan. 21, 2000.*

Chemical Abstracts, vol. 126, No. 7, Feb. 17, 1997, Columbus, Ohio, U.S.; abstract No. 089568, Kai D.W. et al, "Method for Producing 2.2'-bis(diphenylphosphino)-1, 1'binaphthy 1 (BINAP) Derivatives" XP002047609 abstract; and JP 08 311090 A (Merck & Company Incorporated; USA).

Vondenhof, M., "Sulfonic Acid Esters Derived from 1,1'-binaphtalene as New Axially Chiral Photosensitizers", Tetrahedron Letters, vol. 31, No. 7, 1990, pp. 985–988; XP002135636, Elsevier Science Publishers, Amsterdam, NL; ISSN: 0040–4039.

* cited by examiner

*Primary Examiner*—Jean F. Vollano
(74) *Attorney, Agent, or Firm*—Burns, Doane, Swecker & Mathis, L.L.P.

(57) ABSTRACT

The invention concerns a method for preparing a compound of formula (1) wherein: A represents naphthyl or phenyl optionally substituted; and $Ar_1$, $Ar_2$ independently represent a saturated or aromatic carbocyclic group, optionally substituted.

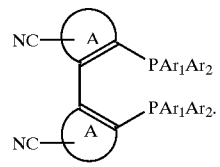

(I)

15 Claims, No Drawings

METHOD FOR PREPARING CHIRAL DIPHOSPHINES

This application is a 371 of PCT/FR00/00083 filed Jan. 14, 2000, now WO00/49028.

The invention relates to a process for preparing chiral diphosphines that are useful as bidentate ligands in the synthesis of catalysts based on transition metals intended for asymmetric catalysis.

Asymmetric catalysis has developed considerably in recent years. It has the advantage of leading directly to the preparation of optically pure isomers by asymmetric induction without it being necessary to resolve racemic mixtures.

2,2'-Bis(diphenylphosphino)-1,1'-binaphthyl (BINAP) is an example of a diphosphorus ligand commonly used to prepare metal complexes for the asymmetric catalysis of hydrogenation, carbonylation and hydrosilylation reactions, C—C bond forming reactions (such as allylic substitutions or Grignard cross-couplings) or even asymmetric isomerization reactions of allylamines.

The development of novel chiral ligands is desirable so as to improve the enantioselectivity of the reactions and, more generally, the general conditions for carrying out these reactions.

The present invention more specifically provides a process for preparing diphosphorus bidentate chiral ligands of 2,2'-bis(diarylphosphino)-1,1'-binaphthyl and 2,2'-bis(diarylphosphino)-1,1'-biphenyl type that are functionalized on the binaphthyl or biphenyl groups, respectively. These ligands, coordinated to transition metals such as ruthenium or rhodium, form complexes that are useful in the asymmetric catalysis of various reactions and more particularly of asymmetric hydrogenation reactions.

The ligands prepared according to the process of the invention are in particular the dicyano derivatives of formula I:

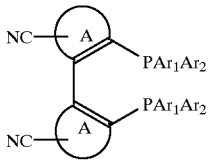

I in which:

A represents phenyl or naphthyl; and $Ar_1$ and $Ar_2$ independently represent a saturated or aromatic carbocyclic radical.

In the context of the invention, the phenyl and naphthyl radicals are optionally substituted.

According to the invention, the term "carbocyclic radical" means an optionally substituted, preferably $C_3$–$C_{50}$ monocyclic or polycyclic radical. Preferably it is a $C_3$–$C_{18}$ radical, which is preferably mono-, bi- or tricyclic.

The carbocyclic radical may comprise a saturated portion and/or an aromatic portion.

When the carbocyclic radical comprises more than one cyclic nucleus (in the case of polycyclic carbocycles), the cyclic nuclei may be fused in pairs or attached in pairs via σ bonds.

Examples of saturated carbocyclic radicals are cycloalkyl groups.

Preferably, the cycloalkyl groups are saturated cyclic hydrocarbon-based radicals that are preferably $C_3$–$C_{18}$ and better still $C_3$–$C_{10}$, and in particular cyclopentyl, cyclohexyl, cycloheptyl, cyclooctyl, adamantyl or norbornyl radicals.

Examples of aromatic carbocyclic radicals are ($C_6$–$C_{18}$) aryl groups and in particular phenyl, naphthyl, anthryl and phenanthryl.

The substituents on the phenyl, naphthyl and carbocyclic radicals are such that they do not interfere with the reactions involved in the process of the invention. These substituents are inert under the conditions involved in bromination (step i), esterification (step ii), nucleophilic substitution (step iii) and coupling reactions.

Preferably, the substituents are alkyl or alkoxy groups.

The term "alkyl" means a saturated, linear or branched hydrocarbon-based radical containing in particular up to 25 carbon atoms and, for example, from 1 to 12 carbon atoms and better still from 1 to 6 carbon atoms.

Examples of alkyl groups are methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 2-ethylbutyl, l-methyl-1-ethylpropyl, heptyl, 1-methylhexyl, 1-propylbutyl, 4,4-dimethylpentyl, octyl, 1-methylheptyl, 2-ethylhexyl, 5,5-dimethylhexyl, nonyl, decyl, 1-methylnonyl, 3,7-dimethyloctyl and 7,7-dimethyloctyl radicals.

In a particularly advantageous manner, the dicyano derivatives of formula I are such that:

represents naphthyl or phenyl, optionally substituted with one or more radicals chosen from ($C_1$–$C_6$)alkyl and ($C_1$–$C_6$) alkoxy; and $Ar_1$ and $Ar_2$ independently represent a phenyl group optionally substituted with one or more ($C_1$–$C_6$)alkyl or ($C_1$–$C_6$)alkoxy; or a ($C_4$–$C_8$)cyclcoalkyl group optionally substituted with one or more ($C_1$–$C_6$)alkyl groups.

Examples of preferred alkyl groups are, in particular, methyl, ethyl, propyl, isopropyl, butyl, isobutyl, t-butyl, pentyl, isopentyl, neopentyl, 2-methylbutyl, l-ethylpropyl, hexyl, isohexyl, neohexyl, 1-methylpentyl, 3-methylpentyl, 1,1-dimethylbutyl, 1,3-dimethylbutyl, 2-ethylbutyl and 1-methyl-1-ethylpropyl.

Advantageously, the alkyl radical contains from 1 to 4 carbon atoms.

The term "alkoxy" denotes an —O-alkyl radical in which alkyl is as defined above.

Advantageously, the cycloalkyl groups are chosen from cyclobutyl, cyclopentyl, cyclohexyl, cycloheptyl and cyclooctyl.

It should be understood that, according to the invention, each of the naphthyl and phenyl groups representing A may be substituted.

Among the ligands of formula I that are preferred are those for which $Ar_1$ and $Ar_2$ are, independently, phenyl optionally substituted with methyl or tert-butyl; or ($C_5$–$C_6$) cycloalkyl optionally substituted with methyl or tert-butyl.

The compounds that are most particularly preferred are those of formula I in which $Ar_1$ and $Ar_2$ are identical. A clearly preferred meaning of $Ar_1$ and $Ar_2$ is optionally substituted phenyl.

Moreover, it is preferred for A to represent naphthyl optionally substituted with one to five and preferably one to two groups chosen from ($C_1$–$C_6$)alkyl and ($C_1$–$C_6$)alkoxy. Better still, A represents unsubstituted naphthyl.

When A represents optionally substituted phenyl, it is preferred for this phenyl to be substituted in the meta position relative to the group $PAr_1Ar_2$ with ($C_1$–$C_6$)alkyl or ($C_1$–$C_6$)alkoxy and better still with methyl or methoxy, the other positions of the phenyl radical being unsubstituted.

One group of compounds that is more particularly preferred consists of the compounds of formula I with a $C_2$ axis of symmetry, with the exclusion of any element of symmetry.

The notion of the $C_2$ axis of symmetry is described in "Elements of Stereochemistry", Wiley, New York, 1969 and in "Advanced Organic Chemistry", Jerry March, Stereochemistry, Chapter 4.

Among this last group of preferred compounds especially distinguished are the compounds of formulae Ia and Ib below:

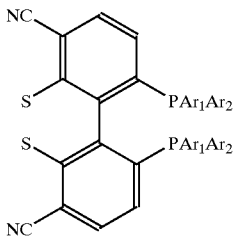

Ia in which $Ar_1$ and $Ar_2$ are as defined above and S represents a substituent which is compatible with the reactions involved, and in particular alkyl or alkoxy, which is preferably $C_1-C_6$,

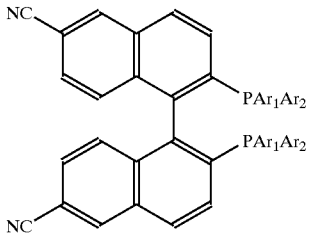

Ib in which $Ar_1$ and $Ar_2$ are as defined above.

The process of the invention more specifically comprises the steps consisting in:

i) brominating a diol of formula II:

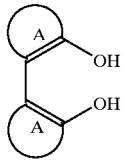

II in which A is as defined above, using a suitable brominating agent so as to obtain a dibromo compound of formula III:

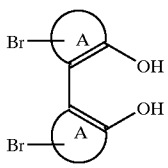

III in which A is as defined above;

ii) esterifying the compound of formula III obtained in the preceding step by the action of a sulfonic acid or an activated form thereof, so as to obtain the corresponding disulfonate;

iii) substituting the two bromine atoms with cyano groups by reacting the disulfonate obtained in the preceding step with a suitable nucleophilic agent so as to obtain the corresponding nitrile;

iv) coupling a phosphine of formula VI:

$$XPAr_1Ar_2 \qquad \text{VI}$$

in which X represents a hydrogen atom or a halogen atom and $Ar_1$ and $Ar_2$ are as defined above, with the nitrile obtained in the preceding step, in the presence of a catalyst based on a transition metal, so as to obtain the expected compound of formula I.

In step (i), the phenyl or naphthyl nucleus, respectively, of the diol of formula II is brominated by the action of a suitable brominating agent.

When A is an unsubstituted phenyl nucleus or a nucleus bearing a substituent in the meta position relative to the OH group, such as $(C_1-C_6)$alkyl or $(C_1-C_6)$alkoxy, the corresponding diol of formula IIa:

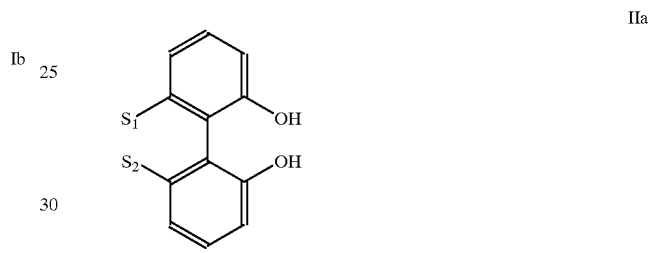

IIa in which $S_1$ and $S_2$ are as defined for S above or independently represent a hydrogen atom or an alkyl or alkoxy group, which is preferably $C_1-C_6$, gives the corresponding bromo compound of formula IIIa:

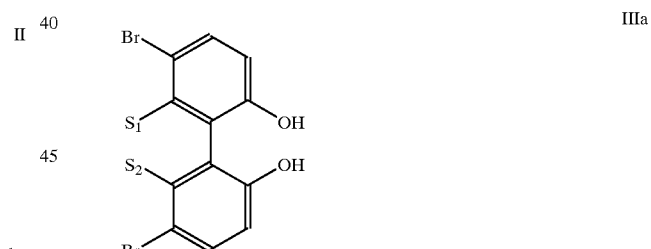

IIIa in which $S_1$ and $S_2$ are as defined above.

When A is a naphthyl nucleus, the bromination of the corresponding diol of formula IIb:

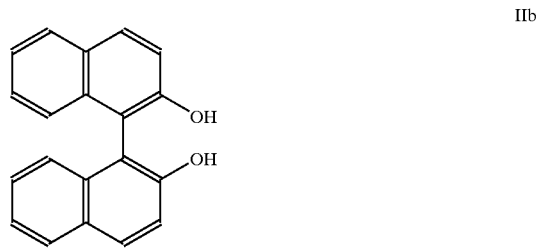

IIb gives compound IIIb below:

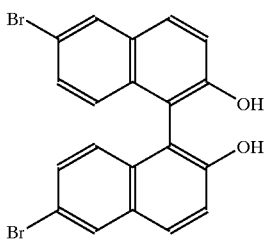

More generally, the hydroxyl groups present on the phenyl and naphthyl nuclei orient the electrophilic reaction such that the position of the bromine atoms on these nuclei is well defined.

The bromination reaction of phenyl or naphthyl nuclei is an electrophilic reaction which is readily performed by the action of $Br_2$ on the corresponding diol.

This reaction may be carried out in the presence of a catalyst such as a Lewis acid and in particular iron chloride. However, since the hydroxyl groups present on the phenyl and naphthyl nuclei activate these nuclei, the bromination is readily performed in the absence of any catalyst.

The diols of formula II are so reactive that it is desirable to carry out the bromination at low temperature, for example between −78° and −30° C. and preferably between −78 and −50° C.

According to one preferred embodiment of the invention, the bromination takes place in an inert aprotic solvent such as a haloaromatic hydrocarbon (for example chlorobenzene or dichlorobenzene); a nitroaromatic hydrocarbon such as a nitrobenzene; an optionally halogenated aliphatic hydrocarbon such as hexane, heptane, methylene chloride, carbon tetrachloride or dichloroethane; or an alicyclic hydrocarbon.

In general, aromatic hydrocarbons with electron-poor aromatic nuclei, i.e. nuclei bearing one or more electron-withdrawing substituents, may be used.

Preferred solvents which may be mentioned are haloaliphatic hydrocarbons and in particular methylene chloride.

As a variant, it is possible to perform the process in glacial acetic acid as solvent. Under these conditions, a solution of bromine in acetic acid is generally added dropwise to a solution of the diol II in acetic acid.

Whether the process is performed in the presence or absence of acetic acid, an excess of the brominating agent relative to the diol II is used.

Preferably, the molar ratio of the brominating agent to the diol II ranges between 2 and 5 and better still between 2 and 3.

When the process is performed in solution, the concentration of the reagents may vary within a very wide range between 0.01 and 10 mol/l, for example between 0.05 and 1 mol/l.

In step (ii), the hydroxyl functions of the diol III are esterified by the action of a sulfonic acid or an activated form thereof, so as to obtain the corresponding disulfonate.

According to the invention, the nature of the sulfonic acid used is not a deciding factor per se.

Advantageously, the sulfonic acid has the formula:

P—SO$_2$—OH in which P represents a hydrocarbon-based aliphatic group; an aromatic carbocyclic group; or an aliphatic group substituted with an aromatic carbocyclic group.

The expression "hydrocarbon-based aliphatic group" means in particular an alkyl group as defined above, which is optionally substituted. The nature of the substituent is such that it does not react under the conditions of the esterification reaction. A preferred example of a substituent for an alkyl group is a halogen atom such as fluorine, chlorine, bromine or iodine.

The expression "aromatic carbocyclic group" means mono- or polycyclic aromatic groups and in particular the mono-, bi- or tricyclic groups defined above, and for example phenyl, naphthyl, anthryl or phenanthryl.

The aromatic carbocyclic group is optionally substituted. The nature of the substituent is not critical provided that it does not react under the esterification conditions. Advantageously, the substituent is optionally halogenated alkyl, alkyl being as defined above and halogen representing chlorine, fluorine, bromine or iodine, and preferably chlorine. As an example, "optionally halogenated alkyl" denotes perfluoroalkyl such as trifluoromethyl or pentafluoroethyl.

According to one preferred embodiment of the invention, the sulfonic acid has the formula:

P—SO$_2$—OH in which P represents $(C_6-C_{10})$aryl optionally substituted with one or more optionally halogenated $(C_1-C_6)$alkyl; optionally halogenated $(C_6-C_{10})$alkyl; or $(C_6-C_{10})$aryl $(C_1-C_6)$alkyl in which the aryl group is optionally substituted with one or more optionally halogenated $(C_1-C_6)$alkyl and the alkyl group is optionally halogenated.

Suitable examples of such sulfonic acids are paratoluenesulfonic acid, methanesulfonic acid and trifluoromethanesulfonic acid, the latter being particularly preferred.

According to one preferred embodiment of the invention, an activated derivative of the sulfonic acid is used. The term "activated derivative" denotes a sulfonic acid in which the acid function —SO$_3$H is activated, for example by formation of an anhydride bond or an —SO$_3$Cl group.

One sulfonic acid derivative which is particularly advantageous is the symmetrical anhydride of trifluoromethanesulfonic acid, of formula $(CF_3-SO_2)_2O$.

When the sulfonic acid has the formula P—SO$_3$H above or is an activated form of this acid, the disulfonate obtained after step ii) corresponds to formula IV:

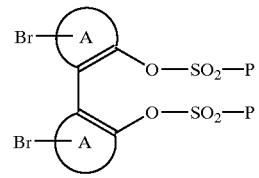

in which A and P are as defined above.

The conditions of the esterification reaction will be readily developed by those skilled in the art. These conditions depend in particular on the nature of the esterifying agent. When the esterifying agent is a sulfonic acid, a higher reaction temperature, of between 20 and 100° C., may prove to be necessary. Conversely, starting with an activated form of this acid, such as an anhydride or a sulfonyl chloride, a lower temperature may be suitable. Generally, a temperature of between −30° C. and 50° C. and preferably between −15° C. and 20° C. may suffice in this case.

The esterification is preferably carried out in a solvent. Suitable solvents are, in particular, optionally halogenated aliphatic, aromatic or cyclic hydrocarbons, such as those defined above. Mention may be made of carbon tetrachloride and dichloromethane. Dichloromethane is particularly preferred. Ethers may also be used as solvent. Mention will be made, for example, of $C_1$–$C_6$ dialkyl ethers (diethyl ether and diisopropyl ether), cyclic ethers (tetrahydrofuran and dioxane), dimethoxyethane and diethylene glycol dimethyl ether.

When the esterifying agent is an activated form of a sulfonic acid, it is desirable to introduce a base into the reaction medium. Examples of bases are N-methylmorpholine, triethylamine, tributylamine, diisopropylethylamine, dicyclohexylamine, N-methylpiperidine, pyridine, 2,6-dimethylpyridine, 4-(1-pyrrolidinyl)pyridine, picoline, 4-(N,N-dimethylamino)-pyridine, 2,6-di-t-butyl-4-methylpyridine, quinoline, N,N-dimethylaniline and N,N-diethylaniline.

Preferred bases which will be essentially selected are pyridine and 4-dimethylaminopyridine.

The reaction may also be performed in a two-phase mixture of water and of an organic solvent such as a haloaliphatic hydrocarbon (for example carbon tetrachloride). In this case, it is preferable to use an esterifying agent in anhydride form and to perform the process in the presence of a water-soluble base such as KOH, NaOH or $K_2CO_3$, preferably KOH.

The reaction of the sulfonic acid or the activated derivative thereof with the bromo diol III is stoichiometric. Nevertheless, it is preferable to perform the process in the presence of an excess of the acid or the activated form thereof. Thus, a ratio of the acid, optionally in activated form, to the diol III of between 2 and 5 and better still between 2 and 3 is recommended.

When the reaction is performed in solution, the concentration of the reagents, which is not a critical parameter according to the invention, may range between 0.1 and 10 mol/l and advantageously between 1 and 5 mol/l.

Those skilled in the art may be inspired by the operating conditions illustrated in J. Org. Chem., vol. 58, No. 7, 1993, 1945–1948 and Tetrahedron setters, vol. 31, No. 7, 985–988, 1990 for carrying out the esterification.

The following step (iii) is a nucleophilic substitution. The two bromine atoms borne by the nuclei A are displaced with cyano groups by the action of a suitable nucleophilic agent.

So as to perform this substitution, those skilled in the art may use any of the methods known in the art.

According to one preferred embodiment of the invention, the nucleophilic agent used is copper cyanide.

The molar ratio of the copper cyanide to the disulfonate is preferably greater than 2 and may advantageously range between 2 and 4 and preferably between 2 and 3.

The reaction is preferably carried out in a solvent. Examples of solvents which may be mentioned are amides such as formamide, dimethylformamide, dimethylacetamide, 2-N-methylpyrrolidinone and hexamethylphosphorylamide. Dimethylformamide is clearly preferred. Pyridine is also a suitable solvent. The reaction temperature is advantageously maintained between 50 and 200° C., for example between 70 and 190° C. and better still between 80 and 180° C.

A temperature which is more particularly suitable is between 100 and 190° C.

The concentration of the reagents in the reaction medium generally ranges between 0.1 and 10 mol/l, for example between 2 and 7 mol/l.

The isolation of the nitrile involves decomposing the intermediate complex formed and trapping the excess cyanide.

The hydrolysis of the intermediate complex may be performed either by the action of hydrated iron chloride or by the action of aqueous ethylenediamine.

In the first case, the reaction medium is poured into an aqueous 50–80% (g/ml) iron chloride solution containing concentrated hydrochloric acid. The resulting solution is heated at 40–80° C. until the complex has completely decomposed. The medium is then separated out by settling and extracted conventionally.

In the second case, the reaction medium is poured into an aqueous ethylenediamine solution (ethylenediamine/water: 1/5–1/1 (v/v), for example 1/3) and the mixture is then stirred vigorously. The medium is then separated by settling of the phases and extracted in a manner which is known per se.

Those skilled in the art may be Inspired by the work of L. Friedman et al. published in J.O.C. 1961, 26, 1522, fur isolating the nitrile.

Starting with the disulfonate of formula IV mentioned above, the product obtained at the end of this step is the nitrile or formula V:

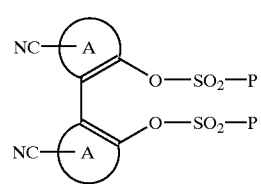

in which A and P are as defined above and the position of the cyano group on the nucleus A is the same as that of the bromine in compound IV.

In the following step (iv), a cross-coupling of a phosphine of formula VI:

$$XPAr_1Ar_2 \qquad\qquad VI$$

in which X is a halogen or hydrogen atom and $Ar_1$ and $Ar_2$ are as defined above, is carried out with the nitrile obtained in the above step, in the presence of a catalyst based on a transition metal.

This coupling leads directly to the expected compound of formula I.

Examples of suitable catalysts are catalysts based on nickel, palladium, rhodium, ruthenium or platinum or on a mixture of these metals.

The preferred catalysts are nickel-based catalysts such as those chosen from $NiCl_2$; $NiBr_2$; $NiCl_2(dppp)$; $NiCl_2(dppb)$; $NiCl_2(dppf)$; $NiCl_2(dppe)$; $NiCl_2(PPh_3)_2$; $Ni(CO)_2(PPh_3)_2$; $Ni(PPh_3)_4$ and $Ni[P(PhO)_3]_4$ in which dppe means (diphenylphosphino)ethane, dppp means (diphenylphosphino) propane, dppb means (diphenylphosphino) butane and dppf means (diphenylphosphino)ferrocenyl.

Among these catalysts, $NiCl_2(dppe)$ is preferred.

The reaction is generally carried out at a temperature of from 50 to 200° C. and preferably from 80 to 130° C.

The molar ratio of compound VI to the nitrile is at least 2. It generally ranges between 2 and 4, for example between 2 and 3.

The amount of catalyst is preferably such that the molar ratio of the nitrile to the catalyst ranges between 5 and 100 and in particular between 5 and 80.

The reaction is preferably performed in a polar aprotic solvent and in particular an amide such as those mentioned above. In this case also, N,N-dimethyl-formamide is preferred. Nevertheless, other types of polar solvent may be used, such as ($C_1$–$C_6$)alkanols (ethanol) aromatic hydrocarbons (toluene, xylene and benzene), ethers (dioxane) and acetonitrile.

The precise reaction conditions depend on the nature of the compound of formula VI involved in the reaction.

When compound VI is $HPAr_1Ar_2$, the reaction is advantageously performed in the presence of a base.

Bases that are particularly suitable are pyridine, 4-dimethylaminopyridine, 2,6-di-tert-butylpyridine, 1,8-diazabicyclo[5.4.0]undec-7-ene (DBU), 1,5-diazabicyclo[4.3.0]non-5-ene (DBN) and 1,4-diazabicyclo-[2.2.2]octane (DABCO or triethylenediamine). DABCO will advantageously be used as base. In this case, it is preferred for the molar ratio of the nitrile to the catalyst to be between 5 and 20, for example between 7 and 15.

When the compound of formula VI is $halPAr_1Ar_2$ in which hal is a halogen atom, preferably Cl or Br (better still Cl), it is necessary to add zinc to the reaction medium.

The amount of zinc is preferably such that the molar ratio of the zinc to the $halPAr_1AR_2$ ranges between 1 and 2 and preferably between 1.2 and 1.7.

In this case, it is desirable to cool the reaction mixture containing the solvent, the nitrile and compound VI to a temperature of between −10° C. and 20° C. throughout the addition of the zinc to the reaction medium. Then, the reaction takes place by heating to a suitable temperature of between 50° C. and 200° C.

When the compound of formula VI is $halPAr_1Ar_2$, it is preferred for the molar ratio of the nitrile to the catalyst to be between 40 and 80, for example between 50 and 70.

For further details regarding the implementation of these coupling reactions, those skilled in the art will refer to D. Cai et al. J.O.C. 1994, 59, 7180 and D. J. Ager et al. Chem. Comm. 1997, 2359.

When A represents phenyl which is optionally substituted, preferably with ($C_1$–$C_6$) alkyl or ($C_1$–$C_6$)alkoxy, the compound obtained after step (iv) has the formula Ic:

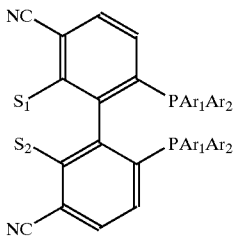

in which $Ar_1$, $Ar_2$, $S_1$ and $S_2$ are as defined above for formula IIa.

When A represents naphthyl, the compound obtained after step (iv) has the formula Ib:

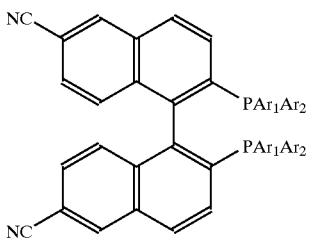

in which $Ar_1$ and $Ar_2$ are as defined above.

The compounds of formula I are ligands capable of coordinating to transition metals such as ruthenium and rhodium. When combined with these metals, the ligands form complexes that are useful in the asymmetric catalysis of enantioselective hydrogenation reactions starting with varied substrates such as β-keto esters, α-keto esters and dehydroamino acids.

The present invention moreover provides a process for converting the compounds of formula I (which contain two cyano functions) into corresponding diaminomethyl compounds.

As a variant, it is possible to convert the two cyano functions of the compounds of formula I into carboxylic acid, imine, hydroxymethyl or amide functions.

The products resulting from these conversions are also ligands which may be used in asymmetric catalysis.

Thus, according to another of its aspects, the invention relates to a process comprising, in addition to steps (i) to (iv) defined above, the step consisting in reducing the nitrile function of the compound of formula I by the action of a reducing agent so as to obtain a compound of formula VII:

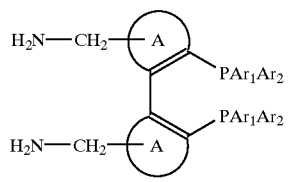

in which A, $Ar_1$ and $Ar_2$ are as defined above.

A suitable reducing agent is lithium aluminum hydride ($LiAlH_4$).

The invention is not intended to be limited to the use of this particular reducing agent.

The reaction is preferably carried out in a solvent or a mixture of solvents.

When the reducing agent is $LiAlH_4$, the solvent advantageously comprises one or more aromatic hydrocarbons (such as benzene, toluene or xylene) mixed with one or more ethers.

Ethers which may be mentioned are $C_1$–$C_6$ alkyl ethers (diethyl ether and diisopropyl ether), cyclic ethers (dioxane and tetrahydrofuran), dimethoxyethane and diethylene glycol dimethyl ether.

Cyclic ethers such as tetrahydrofuran are preferred.

When the reducing agent is $LiAlH_4$, a mixture of toluene and tetrahydrofuran in proportions ranging between (v/v) 70–50/30–50:toluene/tetrahydrofuran (for example 60/40:toluene/THF) will be chosen more preferably.

The reduction may be carried out at a temperature of between 20° C. and 100° C. and preferably between 40° C. and 80° C.

A large excess of the reducing agent is usually used. Thus, the molar ratio of the reducing agent to the compound of formula I generally ranges between 1 and 30, for example between 2 and 20 and in particular between 5 and 18.

The concentration of the reagents in the medium is variable; it may be maintained between 0.005 and 1 mol/l.

The compounds of formula VII obtained according to the process of the invention are novel and form another subject of the invention. Among these compounds, preference is given to those for which A represents naphthyl, which correspond to the following formula:

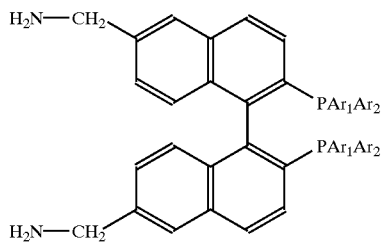

VIIa in which Ar$_1$ and Ar$_2$ are as defined in claim 1.

A preferred group of these diamines consists of the compounds of formula VIIa in which Ar$_1$ and Ar$_2$ are independently chosen from phenyl optionally substituted with methyl or tert-butyl; and (C$_5$–C$_6$)cycloalkyl optionally substituted with methyl or tert-butyl.

Better still, preference is given to the compounds in which Ar$_1$ and Ar$_2$ are identical and represent optionally substituted phenyl.

As a variant, the invention provides a process comprising, in addition to steps (i) to (iv) defined above, the step consisting in treating the compound of formula I in a acidic medium or in basic medium, so as to obtain the corresponding carboxylic acid of formula VIII:

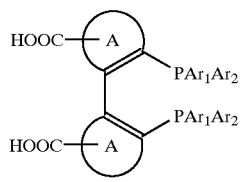

VIII in which A, Ar$_1$ and Ar$_2$ are as defined above.

The conversion of a nitrile function into a carboxylic acid function is described in organic chemistry textbooks. Thus, those skilled in the art can readily determine the appropriate reaction conditions.

One simple way of performing the process consists in using aqueous sodium hydroxide as hydrolysis agent.

The process of the invention may be carried out starting with an optically active compound II with conservation of the chirality from the start to the end of the synthesis.

With the aim of conserving the chirality, the esterification of the compound of formula III will be carried out under anhydrous conditions in the presence of suitable bases chosen from N-methylmorpholine, triethylamine, tributylamine, diisopropylethamine, dicyclohexylamine, N-methylpiperidine, pyridine, 2,6-dimethylpyridine, 4-(1-pyrrolidinyl)pyridine, picoline, 4-(N,N-dimethylamino) pyridine, 2,6-di-t-butyl-4-methylpyridine, quinoline, N,N-dimethylaniline and N,N-diethylaniline.

Thus, starting with a (S)-2,2'-dihydro-1,1'-binaphthyl, (S)-6,6'-dibromo-2,2'-dihydroxy-1,1'-binaphthyl and (S)-6, 6'-dicyano-2,2'-bis(diarylphosphino)-1,1'-binaphthyl are successively obtained.

The same process applied to (R)-2,2'-dihydroxy-1,1'-binaphthyl gives (R)-6,6'-dicyano-2,2'-bis (diarylphosphino)-1,1'-binaphthyl.

The optically active isomers of the compounds of formula II are conventionally isolated from the corresponding racemic mixtures. An optically active resolving agent is usually Used to do this.

In the case of 1,1'-bis(2-naphthol), the enantiomers may be resolved by forming an inclusion complex with (R,R)-1,2-cyclohexanediamine, (R,R) or (S,S)-2,3-(+)-dimethoxy-N,N,N',N'-tetramethylsuccinamide or alternatively (R,R) or (S,S)-2,3-(+)-N,N,N',N'-tetramethyl-2,2'-dimethyl-1,3-dioxolane-trans-dicarboxamlde. These methods have been described in the literature. Another way of performing the process consists in forming an inclusion complex of 1,1'-bis(2-naphthol) with N-benzylcinchoninium chloride. Using acetonitrile as solvent, only the complex with one of the enantiomers precipitates, thus allowing the two enantiomers to be separated. Reference will be made in this respect to the studies by D. Cai published in Tetrahedron Letters, vol. 36, No. 44, 7991–7994, 1995.

As a variant, it is possible, in order to prepare an optically active compound of formula I, to carry out step a) starting with a racemic diol of formula II, to resolve the bromo derivative obtained of formula III and then to continue the synthesis starting with the appropriate optically active bromo compound III.

The difunctional ligands obtained according to the processes of the invention may be used in the preparation of metal complexes intended for the asymmetric catalysis of hydrogenation reactions, hydrosilylation reactions, hydroboration reactions of unsaturated compounds, epoxidation reactions of allylic alcohols, vicinal hydroxylation reactions, hydrovinylation reactions, hydroformylation reactions, cyclopropanation reactions, isomerization reactions of olefins, polymerization reactions of propylene, addition reactions of organometallic compounds to aldehydes, allylic alkylation reactions, reactions of aldol type, Diels-Alder reactions and, in general, reactions for the formation of C—C bonds (such as allyl substitutions or Grignard cross-couplings).

According to one preferred embodiment of the invention, the complexes are used for the hydrogenation of C═O, C═C and C═N bonds.

The complexes which may be used in reactions of this type are rhodium, ruthenium, palladium, platinum, iridium, cobalt, nickel or rhenium complexes, preferably rhodium, ruthenium, iridium, palladium and platinum complexes. Even more advantageously, rhodium, ruthenium or iridium complexes are used.

Specific examples of said complexes of the present invention are given below, with no limiting nature.

In the following formulae, P represents a ligand according to the invention.

A preferred group of the rhodium and iridium complexes is defined by the formula:

[MeLig$_2$P]Y$_I$      IX in which:

P represents a ligand according to the invention;

Y$_I$, represents a coordinating anionic ligand;

Me represents iridium or rhodium; and

Lig represents a neutral ligand.

Among these compounds, those in which:

Lig represents an olefin containing from 2 to 12 carbon atoms;

Y$_I$ represents a PF$_6^-$, PCl$_6^-$, BF$_4^-$, BCl$_4^-$, SbF$_6^-$, SbCl$_6^-$, BPh$_4^-$, ClO$_4^-$, CN$^-$, CF$_3$SO$_3^-$ or halogen, preferably Cl$^-$ or Br$^-$, anion, a 1,3-diketonate, alkylcarboxylate or haloalkylcarboxylate anion with a lower alkyl (preferably C$_1$–C$_6$) radical, a phenylcarboxylate or phenoxide anion in which the benzene ring may be substituted with lower alkyl (preferably C$_1$–C$_6$) radicals and/or halogen atoms, are particularly preferred.

In formula IX, $Lig_2$ may represent two Lig ligands as defined above or a bidentate ligand such as a linear or cyclic, polyunsaturated bidentate ligand comprising at least two unsaturations.

It is preferred according to the invention for $Lig_2$ to represent 1,5-cyclooctadiene, norbornadiene or for Lig to represent ethylene.

The expression "lower alkyl radicals" generally means a linear or branched alkyl radical containing from 1 to 4 carbon atoms.

Other iridium complexes are those of formula:

$$[IrLigP]Y_I \qquad \qquad X$$

in which Lig, P and Y, are as defined for formula IX.

A preferred group of ruthenium complexes consists of the compounds of formula:

$$[RuY_I^1 Y_I^2 P] \qquad \qquad XI$$

in which:

P represents a ligand according to the invention;

$Y_I^1$ and $Y_I^2$, which may be identical or different, represent a $PF_6^-$, $PCl_6^-$, $BF_4^-$, $BCl_4^-$, $SbF_6^-$, $SbCl_6^-$, $BPh_4^-$, $ClO_4^-$ or $CF_3SO_3^-$ anion, a halogen atom, more particularly chlorine or bromine, or a carboxylate anion, preferably acetate or trfluoroacetate.

Other ruthenium complexes are those corresponding to formula XII below:

$$[RuY_I^3 arPY_I^4] \qquad \qquad XII$$

in which:

P represents a ligand according to the invention;

ar represents benzene, p-methylisopropylbenzene or hexamethylbenzene;

$Y_I^3$ represents a halogen atom, preferably chlorine or bromine;

$Y_I^4$ represents an anion, preferably a $PF_6^-$, $PCl_6^-$, $BF_4^-$, $BCl_4^-$, $SbF_6^-$, $SbCl_6^-$, $BPh_4^-$, $ClO_4^-$ or $CF_3SO_3^-$ anion.

It is also possible to use in the process of the invention palladium-based and platinum-based complexes.

As more specific examples of said complexes, mention may be made, inter alia, of $Pd(hal)_2P$ and $Pt(hal)_2P$ in which P represents a ligand according to the invention and hal represents halogen such as, for example, chlorine.

The complexes comprising a ligand according to the invention and the transition metal may be prepared according to the known processes described in the literature.

The complexes are generally prepared from a precatalyst whose nature varies according to the transition metal selected.

In the case of rhodium complexes, the precatalyst is, for example, one of the following compounds: $[Rh^I(CO)_2Cl]_2$; $[Rh^I(COD)_2Cl]_2$ in which COD denotes cyclooctadiene; or $Rh^I(acac)(CO)_2$ in which acac denotes acetylacetonate.

In the case of ruthenium complexes, precatalysts that are particularly suitable are bis(2-methylallyl)-cycloocta-1,5-dieneruthenium and $[RuCl_2(benzene)]_2$. Mention may also be made of $Ru(COD)$ $(\eta^3\text{-}(CH_2)_2CHCH_3)_2$.

By way of example, starting with bis(2-methylallyl)-cycloocta-1,5-dieneruthenium, a solution or suspension is prepared containing the metallic precatalyst, a ligand and a fully degassed solvent such as acetone (the ligand concentration in the solution or suspension ranging between 0.001 and 1 mol/l), to which is added a methanolic hydrogen bromide solution. The ratio of the ruthenium to the bromine advantageously ranges between 1:1 and 1:4 and preferably between 1:2 and 1:3. The molar ratio of the ligand to the transition metal is itself about 1. It may be between 0.8 and 1.2.

When the precatalyst is $[RuCl_2(benzene)]_2$, the complex is prepared by mixing the precatalyst, the ligand and an organic solvent and optionally maintaining a temperature of between 15° C. and 150° C. for 1 minute to 24 hours, preferably 30° C. to 120° C. for 10 minutes to 5 hours.

Solvents which may be mentioned are aromatic hydrocarbons (such as benzene, toluene and xylene), amides (such as formamide, dimethylformamide, dimethylacetamide, 2-N-methylpyrrolidinone or hexamethylphosphorylamide) and alcohols (such as ethanol, methanol, n-propanol and isopropanol), and mixtures thereof.

Preferably, when the solvent is an amide, in particular dimethylformamide, the mixture of the ligand, the precatalyst and the solvent is heated to between 80° C. and 120° C.

As a variant, when the solvent is a mixture of an aromatic hydrocarbon (such as benzene) with an alcohol (such as ethanol), the reaction medium is heated to a temperature of between 30° C. and 70° C.

The catalyst is then recovered according to the conventional techniques (filtration or crystallization) and used in asymmetric reactions. Nevertheless, the reaction which needs to be catalyzed with the complex thus prepared may be carried out without intermediate isolation of the catalyst complex.

In the text hereinbelow, the case of hydrogenation is described in detail.

The unsaturated substrate, dissolved in a solvent comprising the catalyst, is placed under a pressure of hydrogen.

The hydrogenation is carried out, for example, at a pressure ranging between 1.5 bar and 100 bar, and at a temperature of between 20° C. and 100° C.

The exact implementation conditions depend on the nature of the substrate which needs to be hydrogenated. Nevertheless, in the general case, a pressure of from 20 bar to 80 bar and preferably from 40 bar to 60 bar, and a temperature of from 30° C. to 70° C., are particularly suitable.

The reaction medium may consist of the reaction medium in which the catalyst was obtained. The hydrogenation reaction then takes place in situ.

As a variant, the catalyst is isolated from the reaction medium in which it was obtained. In this case, the reaction medium for the hydrogenation reaction consists of one or more solvents, chosen in particular from $C_1$–$C_5$ aliphatic alcohols such as methanol or propanol and ar. amide as defined above, for example dimethylformamide, optionally mixed with benzene.

When the hydrogenation reaction takes place in situ, it is desirable to add to the reaction medium one or more solvents chosen from those mentioned above, and more particularly one or more aliphatic alcohols.

According to one preferred embodiment, fully degassed methanol and the substrate are added to the reaction medium containing the complex. The amount of methanol, or more generally of solvent, which may be added is such that the concentration of the substrate in the hydrogenation reaction medium is between $1 \times 10^{-3}$ and 10 mol/l and preferably between 0.01 and 1 mol/l.

The molar ratio of the substrate to the catalyst generally ranges from 1/100 to 1/100 000 and preferably from 1/20 to 1/2 000. This ratio is, for example, 1/1 000.

The rhodium complexes prepared from the ligands of the invention are more especially suitable for the asymmetric catalysis of isomerization reactions of olefins.

The ruthenium complexes prepared from the ligands of the invention are more especially suitable for the asymmetric catalysis of hydrogenation reaction of carbonyl bonds, of C=C bonds and of C=N bonds.

As regards the hydrogenation of double bonds, the suitable substrates are of the type such as α,β-unsaturated carboxylic acid and/or α,β-unsaturated carboxylic acid derivatives. These substrates are described in EP 95943260.0.

The α,β-unsaturated carboxylic acid and/or the derivative thereof corresponds more particularly to formula A:

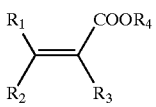

(A)

in which:
R$_1$, R$_2$, R$_3$ and R$_4$ represent a hydrogen atom or any hydrocarbon-based group, provided that:
if R$_1$ is different than R$_2$ and other than a hydrogen atom, then R$_3$ can be any hydrocarbon-based group or functional group denoted by R,
if R$_1$ or R$_2$ represents a hydrogen atom and if R$_1$ is other than R$_2$, then R$_3$ is other than a hydrogen atom and other than —COOR$_4$,
if R$_1$ is identical to R$_2$ and represents any hydrocarbon-based group or functional group denoted by R, then R$_3$ is other than —CH—(R)$_2$, and other than —COOR$_4$,
one of the groups R$_1$, R$_2$ and R$_3$ possibly representing a functional group.

A specific example which may be mentioned, inter alia, is 2-methyl-2-butenoic acid.

A first group of preferred substrates is formed by substituted acrylic acids that are precursors of amino acids and/or derivatives.

The expression "substituted acrylic acids" means the set of compounds whose formula is derived from that of acrylic acid by substituting not more than two of the hydrogen atoms borne by the ethylenic carbon atoms with a hydrocarbon-based group or with a functional group.

They may be symbolized by the following chemical formula:

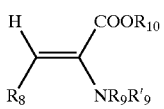

(A1)

in which:
R$_9$ and R'$_9$, which may be identical or different, represent a hydrogen atom, a linear or branched alkyl group containing from 1 to 12 carbon atoms, a phenyl group or an acyl group containing from 2 to 12 carbon atoms, and preferably an acetyl or benzoyl group,
R$_8$ represents a hydrogen atom, an alkyl group containing from 1 to 12 carbon atoms, a cycloalkyl radical containing from 3 to 8 carbon atoms, an arylalkyl radical containing from 6 to 12 carbon atoms, an aryl radical containing from 6 to 12 carbon atoms or a heterocyclic radical containing from 4 to 7 carbon atoms,
R$_{10}$ represents a hydrogen atom or a linear or branched alkyl group containing from 1 to 4 carbon atoms.

Mention may be made more particularly of:
methyl α-acetamidocinnamate,
methyl acetamidoacrylate,
benzamidocinnamic acid,
α-acetamidocinnamic acid.

A second preferred group of substrates consists of itaconic acid and derivatives thereof of formula:

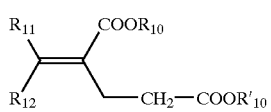

A2 in which:
R$_{11}$ and R$_{12}$, which may be identical or different, represent a hydrogen atom, a linear or branched alkyl group containing from 1 to 12 carbon atoms, a cycloalkyl radical containing from 3 to 8 carbon atoms, an arylalkyl radical containing from 6 to 12 carbon atoms, an aryl radical containing 6 to 12 carbon atoms a heterocyclic radical containing from 4 to 7 carbon atoms,
R$_{10}$ and R'$_{10}$, which may be identical or different, represent a hydrogen atom or a linear or branched alkyl group containing from 1 to 4 carbon atoms.

As more specific examples, mention may be made in particular of itaconic acid and dimethyl itaconate.

A third preferred group of substrates is defined by formula A3:

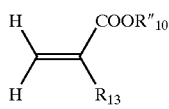

A3 in which:
R"$_{10}$ represents a hydrogen atom or a linear or branched alkyl group containing from 1 to 4 carbon atoms,
R$_{13}$ represents a phenyl or naphthyl group optionally bearing one or more substituents.

Specific examples which may be mentioned are the substrates leading by hydrogenation to 2-(3-benzoylphenyl) proponic acid (Ketoprofen®), 2-(4-isobutylphenyl) propionic acid (Ibuprofen®) and 2-(5-methoxynaphthyl) propionic acid (Naproxen®)

As regards the hydrogenation of carbonyl bonds, the appropriate substrates of ketone type correspond more preferably to formula B:

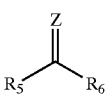

B in which:
R$_5$ is different than R$_6$,
R$_5$ and R$_6$ represent a hydrocarbon-based radical containing from 1 to 30 carbon atoms optionally comprising one or more functional groups,
R$_5$ and R$_6$ can form a ring optionally comprising another hetero atom,
Z is or comprises an oxygen or nitrogen hetero atom or a functional group comprising at least one of these hetero atoms.

These compounds are specifically described in FR 96/08060 and EP 97930607.3.

A first preferred group of such keto substrates has the formula B1:

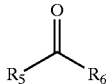

B1 in which:
- $R_5$ is different than $R_6$, the radicals $R_5$ and $R_6$ represent a hydrocarbon-based radical containing from 1 to 30 carbon atoms optionally comprising another ketone and/or acid, ester, thioacid or thioester function;
- $R_5$ and $R_6$ can form a substituted or unsubstituted carbocyclic or heterocyclic ring containing 5 or 6 atoms.

Among these compounds, the ones that are most particularly preferred are the ketones chosen from:

methyl phenyl ketone,
isopropyl phenyl ketone,
cyclopropyl phenyl ketone,
allyl phenyl ketone,
p-methylphenyl methyl ketone,
benzyl phenyl ketone,
phenyl triphenylmethyl ketone,
o-bromoacetophenone,
α-bromoacetone,
α-dibromoacetone,
α-chloroacetone,
α-dichloroacetone,
α-trichloroacetone,
α-chloro-3,3-dichloroacetone
1-chloro-2-oxobutane,
1-fluoro-2-oxobutane,
1-chlorb-3-methyl-2-butanone,
α-chloroacetophenone,
1-chloro-3-phenylacetone,
α-methvlaminoacetone,
α-dimethylaminoacetone,
1-butylamino-2-oxopropane,
1-dibutylamino-2-oxopropane,
1-methylamino-2-oxobutane,
1-dimethylamino-2-oxobutane,
1-dimethylamino-3-methyl-2-oxobutane,
1-dimethylamino-2-oxopentane,
α-dimethylaminoacetophenone,
α-hydroxyacetone,
1-hydroxy-3-methyl-2-butanone,
1-hydroxy-2-oxobutane,
l-hydroxy-2-oxopentane,
l-hydroxy-2-oxohexane,
1-hydroxy-2-oxo-3-methylbutane,
α-hydroxyacetophenone,
1-hydroxy-3-phenylacetone,
α-methoxyacetone,
α-methoxyacetophenone,
α-ethoxyacetone,
α-butoxyacetophenone,
α-chloro-p-methoxyacetophenone,
α-naphthenone,
1-ethoxy-2-oxobutane,
1-butoxy-2-oxobutane,
α-dimethoxyphosphorylacetone,
3-oxotetrahydrothiophene.

Substrates of aldehyde/ketone type containing a second carbonyl group in an α, β, γ or δ position relative to the first carbonyl group are also particularly suitable in the context of the invention. Examples of such diketo compounds are:

α-formylacetone,
diacetyl,
3,4-dioxchexane,
4,5-dioxooctane,
1-phenyl-1,2-dioxopropane,
1-phenyl-2,3-dioxobutane,
diphenyiglyoxal,
p-methoxydiphenylglyoxal,
1,2-cyclopentanedione,
1,2-cyclohexanedione,
acetylacetone,
3,5-heptanedione,
4,6-nonanedione,
5,7-undecadione,
2,4-hexanedione,
2,4-heptanedione,
2,4-octanedione,
2,4-nonanedione,
3,5-nonanedione,
3,5-decanedione,
2,4-dodecanedione,
1-phenyl-1,3-butanedione,
1-phenyl-1,3-pentanedione,
1-phenyl-1,3-hexanedione,
1-phenyl-1,3-heptanedione,
3-methyl-2,4-pentanedione,
1,3-diphenyl-1,3-propanedione,
1,5-diphenyl-2,4-pentanedione,
1,3-bis(trifluoromethyl)-1,3-propanedione,
3-chloro-2,4-pentanedione,
1,5-dichloro-2,4-pentanedione,
1,5-dihydroxy-2,4-pentanedione,
1,5-dibenzyloxy-2,4-pentanedione,
1,5-diamino-2,4-pentanedione,
1,5-bis(methylamlno)-2,4-pentanedione,
1,5-bis(dimethylamino)-2,4-pentanedione,
methyl 3,5-dioxohexanoate,
3-carbomethoxy-2,4-pentanedione,
3-carboethoxy-2,4-pentanedione,
1,3-cyclopentanedione,
1,3-cyclohexanedione,
1,3-cycloheptanedione,
5-carboethoxy-1,3-cyclopentanedione,
2-acetyl-1-cyclopentanone,
2-acetyl-1-cyclohexanone.

As other substrates that are particularly suitable, mention may be made of keto acids or derivatives thereof and keto thioacids or derivatives thereof with a functional group (acid, ester, thioacid or thioester) in an α, β, γ or δ position relative to the carbonyl group. Examples of these are:

2-acetylbenzoic acid,
pyruvic acid,
2-oxobutanoic acid,
3-methyl-2-oxobutanoic acid,
phenylglyoxylic acid,
phenylpyruvic acid,
p-methoxyphenylpyruvic acid,
3,4-dimethoxyphenylpyruvic acid,
methyl acetoacetate,
ethyl acetoacetate,
n-propyl acetoacetate,
isopropyl acetoacetate,
n-butyl acetoacetate,
t-butyl acetoacetate,
n-pentyl acetoacetate,
n-hexyl acetoacetate,
n-heptyl acetoacetate,
n-octyl acetoacetate,
methyl 3-oxopentanoate,
methyl 3-oxohexanoate,
methyl 3-oxohexanoate,
ethyl 3-oxooctanoate,
ethyl 3-oxononanoate,
ethyl 3-oxodecanoate,
ethyl 3-oxoundecanoate,
ethyl 3-oxo-3-phenylpropanoate,
ethyl 4-phenyl-3-oxobutanoate,
methyl 5-phenyl-3-oxopentanoate,
ethyl 3-oxo-3-p-methoxyphenylpropanoate,
methyl 4-chloroacetoacetate,
ethyl 4-chloroacetoacetate,
methyl 4-fluoroacetoacetate,
ethyl 3-trifluoromethyl-3-oxopropanoate,
ethyl 4-hydroxy-3-oxobutanoate,
methyl 4-methoxyacetoacetate,
methyl 4-tert-butoxyacetoacetate,
methyl 4-benzyloxy-3-oxobutanoate,
ethyl 4-benzyloxy-3-oxobutanoate,
methyl 4-amino-3-oxobutanoate,
ethyl 3-methylamino-3-oxobutanoate,
methyl 4-dimethylamino-3-oxobutanoate,
ethyl 4-dimethylamino-3-oxobutanoate,
methyl 2-methylacetoacetate,
ethyl 2-methylacetoacetate,
ethyl 2-chloroacetoacetate,
diethyl 2-acetylsuccinate,
diethyl 2-acetylglutarate,
dimethyl acetylmalonate,
thiomethyl acetoacetate,
thioethyl acetoacetate,
thiophenyl acetoacetate,
methyl pyruvate,
ethyl 3-methyl-2-oxobutanoate,
ethyl phenylglyoxolate,
methyl phenylpyruvate,
ethyl phenylpyruvate,
3-oxobutanoic dimethylamide,
3-oxobutanoic benzylamide,
2-carboethoxycyclopentanone,
2-carboethoxycyclohexanone,
ketopentalacetone,
4-oxopentanoic acid,
4-oxohexanoic acid,
4-oxoheptanoic acid,
4-oxodecanoic acid,
4-oxododecanoic acid,
4-phenyl-4-oxybutyric acid,
4-p-methoxyphenyl-4-oxobutyric acid,
4-(3,4-dimethoxyphenyl)-4-oxobutyric acid,
4-(3,4,5-trimethoxyphenyl)-4-oxobutyric acid,
4-p-chlorophenyl-4-oxybutyric acid,
4-phenyl-4-oxobutyric acid.

It shoulld be noted that when a γ-keto acid or derivative needs to be asymmetrically hydrogenated, the product obtained is generally a γ-butyrolactone derivatIve and, in the case of a δ-keto acid, it is a valerolactone derivative.

Other examples of ketones which may be mentioned, inter alia, are the following monocyclic or polycyclic, saturated or unsaturated cyclic keto compounds:

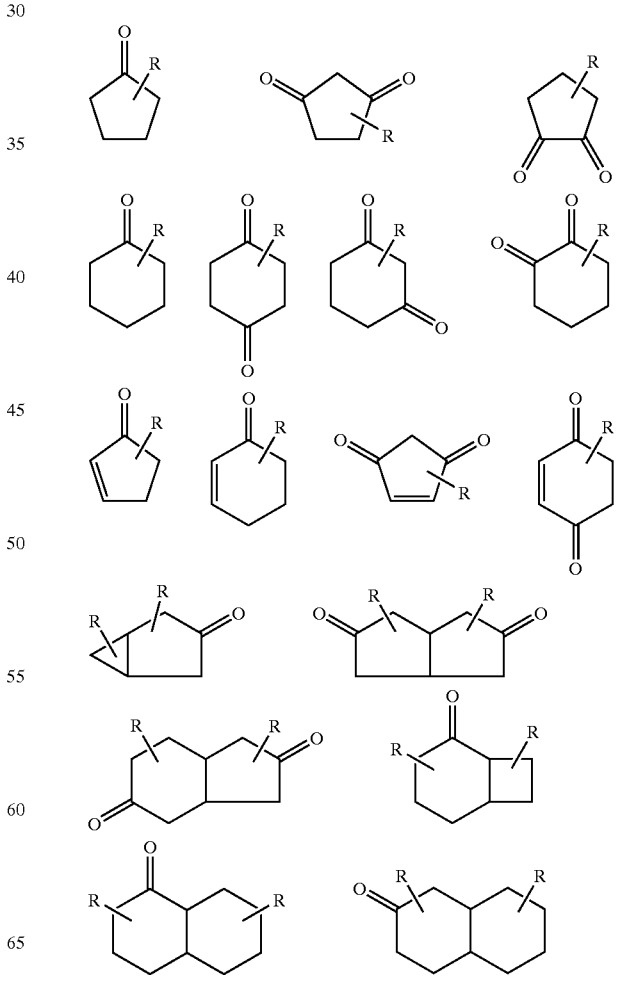

-continued

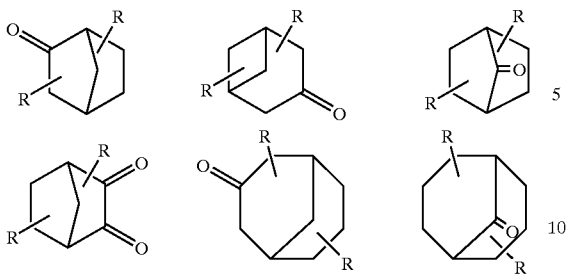

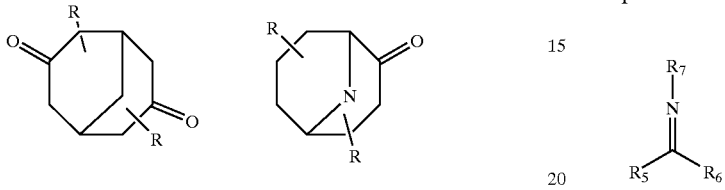

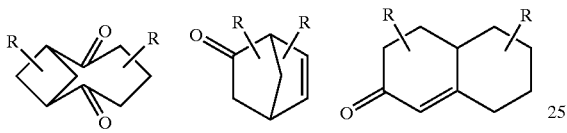

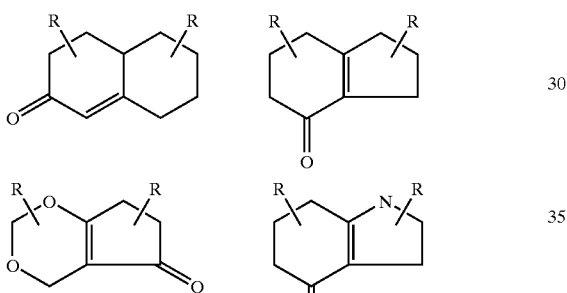

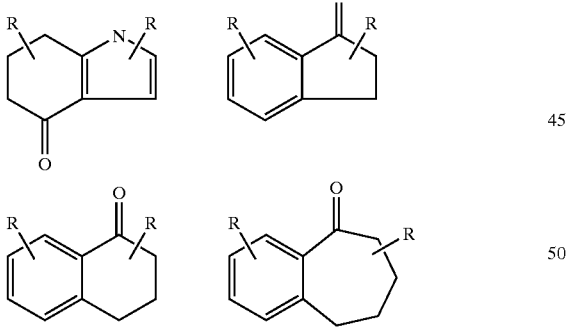

in which R represents a phenyl which is unsubstituted or substituted with alkyl or alkoxy radicals or a halogen atom; or R represents an alkyl or cycloalkyl group which is unsubstituted or substituted with alkyl or alkoxy radicals or a halogen atom, a hydroxyl, ether or amine group; or R represents a halogen atom or a hydroxyl, alkoxy or amine group.

Ketones of steroid type may also be used (for example 3-cholestanone or 5-cholesten-3-one).

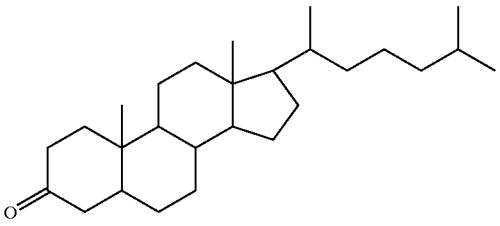

Other keto substrates which may be mentioned are the compounds of formula B2:

B2

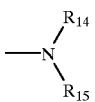

in which:
R$_5$, which is other than R$_6$, have the meaning given above,
R$_7$ represents:
    a hydrogen atom,
    a hydroxyl group,
    a group OR$_{17}$,
    a hydrocarbon radical R$_{17}$,
    a group of formula $$-N\begin{matrix}R_{14}\\R_{15}\end{matrix}$$

a group of formula

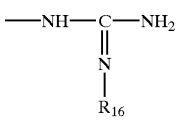

with R$_{14}$, P$_{15}$, R$_{16}$ and R$_{17}$ which represent a hydrogen atom or a hydrocarbon-based group containing from 1 to 30 carbon atoms.

Examples of compounds of formula B2 are:
→N-alkylketoimines, such as:
  N-isobutyl-2-iminopropane
  N-isobutyl-1-methoxy-2-iminopropane
→N-arylalkylketoimines, such as:
  N-benzyl-1-imino-1-(phenyl)ethane
  N-benzyl-1-imino-1-(4-methoxyphenyl)ethane
  N-benzyl-1-imino-1-(2-methoxyphenyl)ethane
→N-arylketoimines, such as:
  N-phenyl-2-iminopentane
  N-(2,6-dimethylphenyl)-2-iminopentane
  N-(2,4,6-trimethylphenyl)-2-iminopentane
  N-phenyl-1-imino-1-phenylethane
  N-phenyl-1-methoxy-2-iminopropane
  N-(2,6-dimethylphenyl)-1-methoxy-2-iminopropane
  N-(2-methyl-6-ethylphenyl)-1-methoxy-2-iminopropane
→compounds of hydrazone type, optionally N-acylated or N-benzoylated:

1-cyclohexyl-1-(2-benzoylhydrazono)ethane,
1-phenyl-1l-(2-benzoylhydrazono)ethane,
1-p-methoxyphenyl-1-(2-benzoylhydrazono)ethane,
1-p-ethoxyphenyl-1-(2-benzoylhydrazono)ethane,
1-p-nitroiphenyl-1-(2-benzoylhydrazono)ethane,
1-p-bromophenyl-1-(2-benzoylhydrazono)ethane,
1-p-carboethoxyphenyl-1-(2-benzoylhydrazono) ethane,
1,2-diphenyl-1-(2-benzoylhydrazono)ethane,
3-methyl-2-(2-p-dimethylaminobenzoylhydrazono) butane,
1-phenyl-1-(2-p-methoxybenzoylhydrazono)ethane,
1-phenyl-1-(2-p-dimethylaminobenzoylhydrazono) ethane,
ethyl 2-(2-benzoylhydrazono)propionate,
methyl 2-(2-benzoylhydrazono)butyrate,
methyl 2-(2-benzoylhydrazono)valerate,
methyl 2-phenyl-2-(2-benzoylhydrazono)acetate.

Other starting substrates are semicarbazones and cyclic keto imines containing an endocyclic or exocyclic bond, such as:

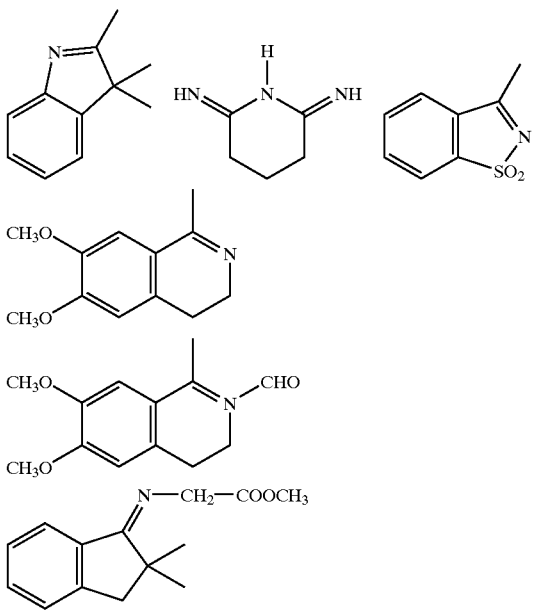

According to one particularly preferred embodiment of the invention, the substrate is a β-keto ester (such as methyl acetoacetate or methyl 3-oxovalerate), an α-keto ester (such as methyl benzoylformate or methyl pyruvate), a ketone (such as acetophenone), an olefin, an unsaturated amino acid or a derivative thereof (in particular an ester thereof).

The complexes obtained from the ligands of formula I and the derivatives thereof give, in particular, good enantioselectivity in hydrogenation reactions.

More particularly, the ruthenium complexes prepared from the ligands obtained according to the process of the invention are suitable for the asymmetric catalysis of hydrogenation reactions of the C=O bonds of β-keto esters.

The ruthenium complexes and ligands of formula VII are particularly suitable for the asymmetric catalysis of hydrogenation reactions of the C=O bonds of ketones.

Thus, according to another of its aspects, the invention relates to the use of a compound of formula I or of formula VII or of formula VIII for the preparation of a metal complex intended for asymmetric catalysis, and more especially a ruthenium, iridium or rhodium complex.

The use of a ligand of formula VII for the preparation of a metal complex and more specifically a ruthenium complex, intended for the asymmetric catalysis of hydrogenation reactions of ketones, forms a preferred subject of the invention.

The examples which follow illustrate the invention more specifically.

PREPARATION 1

Preparation of (S)-6,6'-Dibromo-2,2'-dihydroxy-1,1'-binaphthyl 7.7 g (26.9 mmol) of (S)-2,2'-dihydroxy-1,1'-binaphthyl are dissolved in 145 ml of dichloromethane. The solution is cooled to −75° C. and 3.66 ml of $Br_2$ (71.7 mmol) are then added dropwise over 30 minutes with constant stirring. The solution is stirred for a further 2 and a half hours and then cooled to room temperature. After addition of 180 ml of sodium bisulfite (10% by mass), the organic phase is washed with saturated NaCl solution and dried over $Na_2SO_4$. After evaporating off the solvent, the solid obtained is recrystallized from a toluene/cyclohexane mixture at 80° C. to give 9.8 g (22 mmol, 82% yield) of expected product.

The optical rotation as measured on a Perk-n-Elmer-241 polarimeter (I=10 cm, 25° C., concentration c in $g/dm^3$) is 124.3 at c=1.015 and 578 nm.

For the preparation of the dibromo derivative of the title, reference may be made to G. Dotsevi et al., J. Am. Chem. Soc., 1979, 101, 3035.

PREPARATION 2

Preparation of (S)-6,6'-Dibromo-2,2'-bis (trifloromethanesulfonyloxy)-1,1'-binaphthyl 9.52 g (21.4 mmol) of (S)-6,6'-dibromo-2,2'-dihydroxy-1,1'-binaphthyl are dissolved in a mixture of 40 ml of $CH_2Cl_2$ and 5.4 ml of pyridine. After cooling the mixture to 0° C., 8.7 ml (14.5 g, 51.5 mmol) of triflic anhydride (($CF_3$—$SO_2$)$_2$O) are added slowly. After stirring for 6 h, the solvent is evaporated off and the reaction mass is dissolved in 100 ml of ethyl acetate. After washing with aqueous 5% HCl solution, saturated $NaHCO_3$ solution and saturated NaCl solution, the organic phase is dried over $Na_2SO_4$ and the solvent is then evaporated off under reduced pressure. The yellow oil is purified by chromatography on silica ($CH_2Cl_2$) to give 12.5 g (17.7 mmol, 83% yield) of expected product.

$[\alpha]_D$=151.3° (c=1.005, THF), the optical rotation being measured under the same conditions as in Preparation 1, but at the wavelength corresponding to the D line of sodium.

For the preparation of the title compound, reference also be made to the studies by M. Vondenhof Tetrahedron Letters, 1990, 31, 985.

PREPARATION 3

Preparation of (S)-6,6'-Dibromo-2,2'-bis (trifluoromethanesulfonyloxy)-1,1'-binaphthyl As a variant, the title compound may be prepared from (R)-6,6'-dibromo-2,2'-dihydroxy-1,1'-binaphthyl according to the procedure described below.

10.0 g (22.52 mmol) of (R)-6,6'-dibromo-2,2'-dihydroxy-1,1'-binaphthyl are dissolved in a solution of 6.3 g (0.11 mol) of KOH in 300 ml of degased water. The mixture is cooled to 0° C. and a solution of 11.4 ml (19.1 g, 68 mmol) of triflic anhydride in 200 ml of $CCl_4$ is then added over 45 minutes such that the temperature does not exceed 10° C. After stirring for 30 min, 300 ml of $CH_2Cl_2$ are added. The organic phase is washed with water and then dried over $MgSO_4$. 15.89 g of crude product are then purified by chromatography on silica (1/1 $CH_2Cl_2$/cyclohexane) to give 12.94 g (18.27 mmol, 81% yield) of pure product.

$[\alpha]_D = -153.2°$ (c=0.945, THF), the optical rotation being measured under the same conditions as in Preparation 1, but at the wavelength corresponding to the D line of sodium.

$^1H$ NMR ($CDCl_3$, 200 MHz): δ (ppm): 7.07 (d($J_{H-H}$=7.07), CH, 2H); 7.48 (dd($J^1_{H-H}$=9.05; $J^2_{H-H}$=1.94), CH, 2H); 7.62 (d($J_{H-H}$=9.11), CH, 2H);p 8.06 (d($J_{H-H}$=9.13), CH, 2H); 8.18 (d($J_{H-H}$=1.90), CH, 2H).

$^{13}C$ NMR ($CDCl_3$, 200 MHz); δ (ppm)=118.1 (Cq($J_{C-F}$=320)); 120.2 (Cq); 120.7 (CH); 122.0 (Cq); 123.4 (Cq); 128.2 (CH); 130.5 (CH); 131.4 (CH); 131.6 (Cq); 131.7 (CH); 133.4 (Cq).

PREPARATION 4

Preparation of (S)-6,6'-Dicyano-2,2'-bis (trifluoromethanesulfonyloxy)-1,1'-binaphthyl 12.5 g (17.7 mmol) of the compound prepared in Preparation 2 and 3.5 g (38.8 mmol) of CuCN are stirred at 180° C. in 20 ml of N-methylpyrrolidone for 4 h. After cooling to room temperature, the black suspension is poured into a solution of 15 ml of diaminoethane in 35 ml of water. The solution is extracted several times with 30 ml of $CH_2Cl_2$ and the organic phase is washed with aqueous 10% KCN solution and saturated NaCl solution. After drying over $Na_2SO_4$, the solvent is evaporated off under reduced pressure. The black oil thus obtained s purified by chromatography on silica (9/1 $CH_2Cl_2$/cyclohexane) to give 6.5 g (10.8 mmol, 61% yield) of pure product.

$[\alpha]_D = -171.7°$ (c=1.15, THF), the optical rotation being measured under the same conditions as in Preparation 1, but at the wavelength corresponding to the D line of sodium. $^1H$ NMR ($CDCl_3$, 200 MHz); δ (ppm)=7.30 (d($J_{H-H}$=9.81), CH, 2H); 7.59 (dd($J^1_{H-H}$=8.82, $J^2_{H-H}$=1.65), CH, 2H); 7.78 (d($J_{H-H}$=9.11), CH, 2H); 8.29 (d($J_{H-H}$=8.09), CH, 2H); 8.46 (d($J_{H-H}$=1.29), CH, 2H). $^{13}C$ NMR ($CDCl_3$, 200 MHz): δ (ppm)=111.7 (CN); 118.0 (Cq); 118.1 (Cq($J_{C-F}$=320)); 121.16 (CH); 123.3 (Cq); 127.7 (CH); 128.9 (CH); 131.4 (Cq); 133.2 (CH); 134.4 (Cq); 134.5 (CH); 147.4 (Cq).

For the preparation of the title compound, those skilled in the art may refer to the studies by Friedman et al., J. Org. Chem. 1961, 26, 2522 and M. S. Neuman et al., J. Org. Chem., 1961, 26, 2525.

EXAMPLE 1

Preparation of (S)-6,6'-Dicyano-2,2'-bis (diphenylphosphino)-1,1'-binaphthyl(I: A=Phenyl; $Ar_1=Ar_2$=phenyl)

A solution of $NiCl_2$dppe (371 mg, 0.7 mmol) and of diphenylphosphine (3 ml, 17 mmol) in 14 ml of DMF (anhydrous and degased) is heated for 30 minutes at 100° C. in a 100 ml three-necked round-bottomed flask on which is mounted an argon inlet. (S)-6,6'-Dicyano-2,2'-bis (trifluoromethanesulfonyloxy)-1,1'-binaphthyl (4.4 g, 7.4 mmol) and DABCO (3.375 g, 30 mmol) dissolved in 20 ml of DMF are added dropwise. The reaction medium is left at 100° C. After 1.3 and 7 hours, 0.75 ml of diphenylphosphine is added. The solution is stirred for 2 days. It is then cooled to 0° C. and then filtered under argon and washed with methanol (2×10 ml). Finally, the solid is dried under vacuum to give the expected product in a yield of 50%.

Elemental analysis for $C_{46}H_{30}N_2P_2$; calculated: C=80.88; H=4.43; N=4.10; P=9.07; found: C=81.61; H=4.45; N=4.11; P=8.99. $^1H$ NMR ($CDCl_3$, 200 MHz) δ (ppm): 6.59 (d, 2H, CH); 6.87 (dd, 2H, CH); 6.92–6.99 (m, 4H, CH); 7.09 (t, 4H, CH); 7.17–7.31 (m, 12H, CH); 7.57 (d, 2H, CH); 7.95 (d, 2H, CH); 8.20 (s, 2H, CH). $^{13}C$ NMR ($CDCl_3$, 50 MHz) (ppm): 109.8 (CH); 119.0 (Cq); 126.3 (CH); 127.7 (CH); 128.4 (CH); 128.5 (CH); 128.5 (CH); 128.6 (CH); 128.8 (CH); 129.3 (CH); 132.0 (CH); 132.1 (Cq); 132.9 (CH (triplet $J_{C-P}$=11.7); 133.9 (Cq); 134.1 (Cq); 134.9 (CH (triplet $J_{C-P}$=9.9)); 136.8 (Cq); 140.6 (Cq). $^{31}P$ NMR ($CDCl_3$ 81 MHz) δ (ppm): −12.75.

EXAMPLE 2

Preparation of (S)-6,6'-bis(Aminomethyl)-2,2'-bis (diphenylphosphino)-1,1'-binaphthyl (VII: $Ar_1=Ar_2=C_6H_5$)

557 mg (14.7 mmol) of $LiAlH_4$ are dissolved in a mixture of THF (30 ml)/toluene (60 ml) in a 250 ml round-bottomed flask placed under an argon atmosphere. (S)-6,6'-Dicyano-2,2'-bis(diphenylphosphino)-1,1'-binaphthyl (650 mg, 0.97 mmol) is added to this solution, which is stirred and refluxed for 4 hours. It is then cooled to 0° C. 600 μl of water and 600 μl of 15% NaOH are added. 2 g of Celite are then added and the mixture is filtered through a Millipore filter under argon. 60 ml of dichloromethane are added and the mixture is stirred and filtered again. This operation is carried out three times. The organic phase obtained is washed with saturated aqueous NaCl solution and then dried over $Na_2SO_4$. The solvent is evaporated to give a yellow solid (657 mg, quantitative yield) characterized by NMR (proton, carbon and phosphorus) corresponding to the expected structure.

Elemental analysis for $C_{46}H_{38}N_2P_2$; calculated: C=80.59; H =6.00; N=3.55; P=7.84; found: C=81.14; H=5.51; N=3.13; P=7.90. $^1H$ NMR ($CDCl_3$, 200 MHz) δ (ppm): 1.68 (s, 4H, $NH_2$); 3.81 (s, 4H, $CH_2$); 6.72 (s, 4H, CH); 6.9–7.3 (m, 20H, CH); 7.33 (d, 2H, CH); 7.64 (s, 2H, CH); 7.76 (d, 2H, CH). P NMR ($CDCl_3$, 81 MHz) δ (ppm): −15.08.

EXAMPLE 3

Preparation of a Ruthenium Catalyst

The catalyst is prepared in situ. All the solvents used were rigorously degased and are anhydrous. The reaction medium is maintained under an argon atmosphere. The ligand and the metallic precatalyst, bis(2-methylallyl)cycloocta-1,5-dieneruthenium, in a ligand/metal molar ratio of 1:1, are directly weighed out in a 5 ml conical-based glass reactor taken from the oven and equipped with a stirrer. The reactor is sealed with a septum and the air is flushed out with an argon inlet. Acetone (1 ml) is then added to give a white suspension. This suspension is stirred for 30 minutes and a 0.29 M methanolic HBr solution is then added (Ru/Br ratio of 1/2.3). A change in the color of the solution, which turns brown, is then observed. This solution is stirred for a further 1 hour and the solvent is then evaporated off. The catalyst is thus obtained with the appearance of a brown solid.

Two complexes are prepared according to this procedure.

The first, Dicyano-BINAP, starting with (S)-6,6'-dicyanc-2,2'-bis(diphenylphosphino)-1,1'-binaphthyl (obtained in Example 1).

The second, Diam-BINAP, starting with S)-6,6'-diaminomethyl-2,2'-bis(diphenylphosphino)-1,1'-binaphthyl (obtained in Example 2).

EXAMPLE 4

This example illustrates the hydrogenation of a β-keto ester in the presence of the ruthenium complexes prepared in Example 3.

The hydrogenation protocol is described below:

Methanol which has been predried over magnesium is added (2.5 ml) under argon to the conical reactor in which the catalyst has just been prepared. The substrate is then added (in a given catalyst/substrate ratio). The operation consisting in placing under vacuum and filling the reactor with argon is repeated three times. The septum is then replaced with a pierced stopper and the reactor is then placed in an autoclave. The autoclave is purged three times with argon and then three times with hydrogen, after which 40 bar of hydrogen pressure is applied. The autoclave is placed on a hot plate (50° C.) and stirring is maintained over-night. The conical reactor is finally recovered, the stopper is replaced with a septum and argon is reinjected into this reactor. The reactor is placed in a centrifuge and the solution is then extracted using a syringe. It is placed in a 50 ml round-bottomed flask and diluted with 20 ml of methanol, thus ready to be injected onto a chromatography column for gas chromatography to analyze the degree of conversion and the enatioselectivity of the reaction.

More specifically, the determination of the enantiomeric excesses is carried out by chiral gas chromatography on a column of Macherey-Nagel type (Lipodex A 25 m×0.25 mm).

The test substrate is a β-keto ester, namely methyl acetoacetate. It gives, after hydrogenation, methyl 3-hydroxybutanoate. The compound obtained is the S enantiomer, the catalysts being prepared from the compounds of Examples 1 and 2.

The results obtained for each of the complexes described in Example 3 above are given in Table 1 below:

TABLE 1

| Substrate | Complex | Degree of conversion (%) | Enantiomeric excess (%) |
|---|---|---|---|
| Methyl acetoacetate | Dicyano-BINAP | 25 | 100 |
| Methyl acetoacetate | Diam-BINAP | 100 | 100 |

By way of comparison, the hydrogenation of methyl acetoacetate is carried out in the presence of a ruthenium complex prepared from (R)-2,2'-bis(diphenylphosphino)-1,1'-binaphthyl. The reaction conditions for the hydrogenation and for the preparation of the metal catalyst are as described above. The results obtained are collated in Table 2, it being understood that the hydrogenation product is, in this case, methyl (R)-3-hydroxybutanoate.

TABLE 2
(comparative)

| Substrate | Complex | Degree of conversion (%) | Enantiomeric excess (%) |
|---|---|---|---|
| Methyl acetoacetate | BINAP | 100 | 99 |

As may be seen, the complexes prepared from the compounds of Examples 1 and 2 above give excellent enantiomeric excesses. The catalysts of the invention thus allow a highly enantioselective hydrogenation reaction to be carried out.

EXAMPLE 5

This example illustrates the hydrogenation of an aromatic ketone in the presence of the ruthenium complexes prepared in Example 3.

The hydrogenation protocol followed is as described in Example 4, except that the substrate used is acetophenone. It leads to phenylethanol.

The determination of the enantiomeric excesses is performed under the same conditions as in Example 4.

The results obtained are given in Table 3 below.

TABLE 3

| Complex | Degree of conversion (%) | Enantiomeric excess (%) |
|---|---|---|
| Dicyano-BINAP | 22 | 2 |
| Diam-BINAP | 72 | 18 |

By way of comparison, this same substrate was hydrogenated in the presence of the ruthenium complex with 2,2'-bis(diphenylphosphino)-1,1'-binaphthyl prepared in Example 4.

The hydrogenation reaction conditions are as described above.

The results obtained are a degree of conversion of less than 1% (traces) and an enantiomeric excess of 0%.

This example shows very clearly the superiority of the catalysts of the invention.

What is claimed is:

1. A process for preparing a compound of formula I:

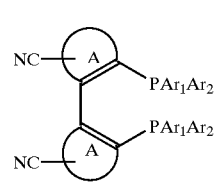

I in which:

A represents an optionally substituted phenyl or naphthyl; and $Ar_1$ and $Ar_2$ independently represent an optionally substituted saturated or aromatic carbocyclic group;

this process comprising the steps comprising:
i) brominating a diol of formula II:

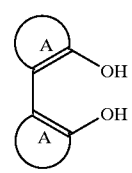

II in which A is as defined above, using a suitable brominating agent so as to obtain a dibromo compound of formula III:

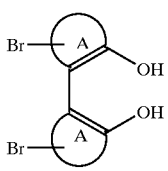

(III)

in which A is as defined above;

ii) esterifying the compound of formula III obtained in the preceding step by the action of a sulfonic acid or an activated form thereof, so as to obtain the corresponding disulfonate;

iii) substituting the two bromine atoms with cyano groups by reacting the disulfonate obtained in the preceding step with a suitable nucleophilic agent so as to obtain the corresponding nitrile;

iv) coupling a phosphine of formula VI:

(VI)

in which X represents a hydrogen atom or a halogen atom and $Ar_1$ and $Ar_2$ are as defined above, with the nitrile obtained in the preceding step, in the presence of a catalyst based on a transition metal, so as to obtain the compound of formula I.

2. The process as claimed in claim 1, wherein:

A represents naphthyl or phenyl, optionally substituted with one or more radicals selected from the group consisting of $(C_1–C_6)$ alkyl and $(C_1–C_6)$alkoxy; and $Ar_1$ and $Ar_2$ independently represent a phenyl group optionally substituted with one or more $(C_1–C_6)$ alkyl or $(C_1–C_6)$ alkoxy; or a $(C_4–C_8)$ cycloalkyl group optionally substituted with one or more $(C_1–C_6)$ alkyl groups.

3. The process as claimed in claim 1, wherein $Ar_1$ and $Ar_2$ are independently selected from phenyl optionally substituted with methyl or tert-butyl; and $(C_5–C_6)$-cycloalkyl optionally substituted with methyl or tert-butyl.

4. The process as claimed in claim 1, wherein $Ar_1$ and $Ar_2$ are identical and represent optionally substituted phenyl.

5. The process as claimed in claim 1, wherein A represents naphthyl.

6. The process as claimed in claim 1, for the preparation of an optically active compound of formula I from an optically active diol of formula II.

7. The process as claimed in claim 1, wherein the bromination is performed, in step (i) by the action of bromine, at a temperature of between −78° C. and −30° C.

8. The process as claimed in claim 1, comprising carrying out, in step (ii), the esterification by the action of trifluoromethanesulfonic anhydride in the presence of a base.

9. The process as claimed in claim 1, wherein the nucleophilic agent used in step (iii) is CuCN.

10. The process as claimed in claim 1, comprising reacting, in step (iv), $HPAr_1Ar_2$ with the nitrile in the presence of [bis(diphenylphosphino)ethane]nickeldichloride and triethylenediamine at a temperature of from 50 to 200° C.

11. The process as claimed in claim 1, comprising reacting, in step (iv), a compound of formula $XPAr_1Ar_2$ (in which X is a halogen atom), with the nitrile in the presence of [bis(diphenylphosphino)ethanenickel]dichloride and zinc, at a temperature of between 50 and 200° C.

12. The process as claimed in claim 10, wherein the molar ratio of compound VI to the nitrile is between 2 and 4.

13. The process as claimed in claim 10, wherein the reaction of the compound of formula VI with the nitrile is carried out in N,N-dimethylformamide as a solvent.

14. The process as claimed in claim 1, also comprising treating the compound of formula I in a basic medium or in an acidic medium to obtain the corresponding carboxylic acid of formula:

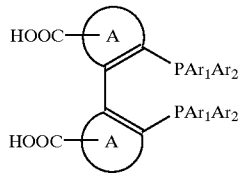

in which A, $Ar_1$ and $Ar_2$ are as defined in claim 1.

15. The process according to claim 8, wherein the base is pyridine or 4-dimethylaminopyridine.

* * * * *